United States Patent [19]

Berke et al.

[11] Patent Number: 4,459,303

[45] Date of Patent: Jul. 10, 1984

[54] ANTIMICROBIAL PRESERVATIVE COMPOUNDS

[75] Inventors: Philip A. Berke, Madison; William E. Rosen, Summit, both of N.J.

[73] Assignee: Sutton Laboratories, Inc., Chatham, N.J.

[21] Appl. No.: 177,136

[22] Filed: Aug. 11, 1980

[51] Int. Cl.$^3$ .................. A01N 43/50; C07D 233/88
[52] U.S. Cl. ................. 424/273 R; 548/310; 548/311
[58] Field of Search ............. 548/310, 311; 424/273 R

[56] References Cited

U.S. PATENT DOCUMENTS

| | | | |
|---|---|---|---|
| 3,248,285 | 4/1966 | Berke | 548/311 X |
| 3,968,250 | 7/1976 | Boucher | 424/333 |
| 3,983,252 | 9/1976 | Buchalter | 424/333 |

FOREIGN PATENT DOCUMENTS 2362131  3/1978  France ................ 548/311

OTHER PUBLICATIONS

Rodd, E. (Editor), *Chemistry of Carbon Compounds*, vol. I, Part A, Elsevier, London, 1951, pp. XIII, XIV, XV, 472, 717.

*Chemical Abstracts*, 88:79149d (1978) [German Ols. 2,718,244, Fellows, 12/8/77].

*Chemical Abstracts*, 82:103184k (1975) [German Ols. 2,324,587, Heiss, 12/5/74].

*Chemical Abstracts*, 70:68369c (1969) [Japan, 68 16,141, Murayama, 7/8/68].

*Chemical Abstracts*, 87:78947e (1977) [Eggensperger H, Hosp.-Hyg., Gesundheitswes. Desinfekt 1977, 69(3), 79-82, 84-85].

*Chemical Abstracts*, 91:194591w (1979) [Japan Kokai 79 81,201, Otsuki, 6/28/79].

*Primary Examiner*—Richard A. Schwartz
*Attorney, Agent, or Firm*—Bacon & Thomas

[57] ABSTRACT

New antimicrobial agents are produced by the reaction of allantoin and glutaraldehyde. Substances which are subject to microbial spoilage are preserved by the addition of these products. They are effective against bacteria, yeasts and molds. Solutions of these new antimicrobial agents can also be used by themselves as disinfectants, sterilants, sanitizers, or embalming fluids.

15 Claims, No Drawings

ANTIMICROBIAL PRESERVATIVE COMPOUNDS

FIELD OF THE INVENTION

This invention relates to the field of antimicrobial compounds, compositions and usages.

DESCRIPTION OF THE PRIOR ART

Allantoin is known to possess soothing properties in preparations for topical use. It has been used alone and in the form of various complexes. See U.S. Pat. Nos. 3,927,021 and 3,970,756 wherein allantoin glycine complexes useful in medicinal and cosmetic preparations are disclosed. It has also been condensed with formaldehyde to provide products having bacteriostatic and/or bactericidal properties. See U.S. Pat. No. 3,248,285. Glutaraldehyde is available as a nonstable solution having germicidal activity but is characterized by irritating properties including a strong odor.

SUMMARY OF THE INVENTION

This invention is concerned with new antimicrobial agents produced by the reaction of allantoin and glutaraldehyde. We have found that if glutaraldehyde and allantoin are reacted under a variety of conditions, a series of new products are obtained which have outstanding antimicrobial activity against bacteria, yeasts and molds. Because of these properties, these compounds are valuable additives in many areas which require protection from the adverse effects of microorganisms.

It is a general object of the present invention to provide novel antimicrobial derivatives of allantoin which, in addition to being useful for bactericidal and/or bacteriostatic purposes are also effective against yeasts and molds. A more specific object of the present invention is to provide antimicrobial derivatives of allantoin produced by the condensation reaction between allantoin and glutaraldehyde.

DETAILED DESCRIPTION OF THE INVENTION

Allantoin is substituted diketotetrahydroimidazole having the formula

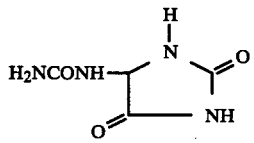

Because of the presence of active hydrogens in different locations, allantoin can react with glutaraldehyde to form a great variety of derivatives, depending on the particular reaction conditions. Thus, the character of the product will be determined by the respective proportions of the reactants, reaction temperature, and the absence or presence of a catalyst. Where a catalyst is used, it can be either basic or acidic.

In one concept (allantoin:glutaraldehyde ratio of 1:1) the reaction between allantoin and glutaraldehyde can be represented, for example, by the following equation:

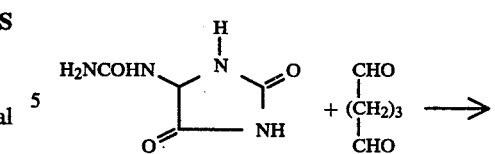

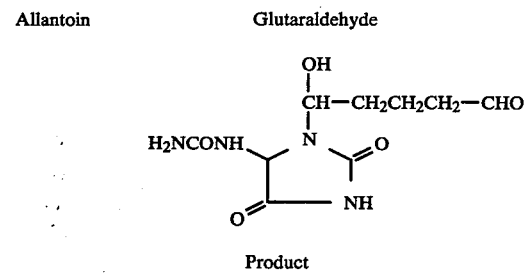

However, since allantoin has four nitrogen atoms which can serve as sites for the reaction with glutaraldehyde, the reaction may occur at a different nitrogen from that shown above and progressively more nitrogen atoms will become involved as the glutaraldehyde to allantoin ratio increases. When they are reacted in a ratio of 4:1, it is possible to obtain a tetra-substituted monomer:

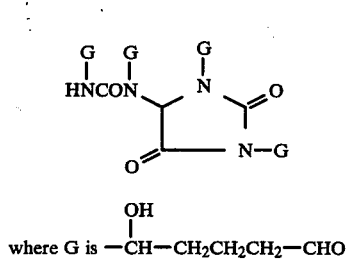

Furthermore, because glutaraldehyde has two reactive aldehyde end groups, both of which can react with nitrogens of the same allantoin molecule or with the nitrogens of different allantoin molecules, it is possible, respectively, to obtain new ring compounds or dimers, trimers, or higher polymers, depending on the relative proportions of the reactants and the reaction conditions.

In the reactions between glutaraldehyde and allantoin, there is initially formed compounds having a carbinolamine group, $$-\overset{|}{N}-CHOH.$$

This group can dehydrate to form

(terminal nitrogen of side chain) or it can polymerize to form repeating units

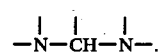

Since dimers and higher polymers can form by this route as well as through the reactive aldehyde end groups, it is possible to obtain products in which the glutaraldehyde to allantoin ratios are, for example, 0.5:1, 1.5:1, 2.5:1, and 3.5:1. Further, since the compounds have weakly acid, as well as weakly basic amine groups, they can form salts with bases and with acids. The alkali metal salts and the sulfates, nitrates, chlorides and phosphates are illustrative. The present invention is intended to include all such possibilities in which the reaction product exhibits antimicrobial activity.

In general, therefore, the invention comprises antimicrobial compounds of the formula:

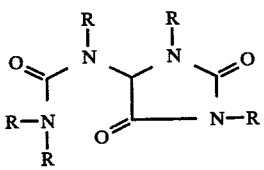

wherein each R is selected from the group consisting of hydrogen and —CHOH(CH$_2$)$_3$CHO, with the proviso that all of the R's are not hydrogen; the carbinolamine dehydration derivatives of said compounds; the dimers and polymers of said compounds; and the salts of said compounds with acids and bases.

In another aspect, the invention comprises compounds of the formula:

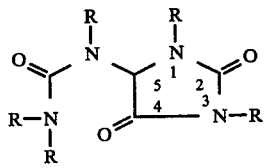

wherein each R is selected from the group consisting of H, —CH.(OH).CH$_2$CH$_2$CH$_2$CHO, —CH(OH).CH$_2$CH$_2$CH(OH)—allantoin, —CH(allantoin)CH$_2$CH$_2$CH$_2$CHO, —CH(allantoin).CH$_2$CH$_2$CH$_2$CH(OH)—allantoin, —CH(allantoin)CH$_2$CH$_2$CH$_2$CH(allantoin)$_2$, again with the proviso that all of the R's are not hydrogen.

The reaction product can, as noted above, be monomeric, dimeric, or polymeric. Since one or both ends of the glutaraldehyde molecule can react with one or two nitrogens of the same or different allantoin molecules, the number of possible reaction products is considerable. Further, when the end of a glutaraldehyde molecule condenses with the same allantoin molecule, both bonds of the terminal

group can be attached to the same or to two different nitrogen atoms. In the former case and when that nitrogen atom has two other groups attached to it, a positive charge arises at the nitrogen atom (e.g.

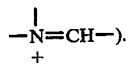

In general, base catalysis favors amine-methylol (i.e. carbinolamine) addition products, and acid catalysis, or omission of a catalyst, favors dimer or polymer formation or dehydration of the amine-methylol to the Schiff base (—N=CH—). The word "condensation" as used herein is used in the broad sense to include addition reactions, ring closure, polymerization, as well as reactions in which water or other substance is eliminated.

Referring once more to the general formula shown above and to the several stated values of the substituent R, since the latter cannot simultaneously be all hydrogens, the monomers in accordance with the present invention can be represented by the general formula in which at least one R is —CH(OH)CH$_2$CH$_2$CH$_2$CHO. The monomers also include those condensation products in which the first reacting or the remaining terminal —CHO group has reacted with the same or a different nitrogen atom on the same allantoin molecule. Accordingly, as used in the claims below, the term "monomer" is intended to include those condensation products in which R is at least one —CH(OH)CH$_2$CH$_2$CH$_2$CHO group and also those condensation products in which the first reacting or the remaining terminal —CHO group of at least one of the glutaraldehyde molecules has reacted with the same or a different nitrogen in the same allantoin molecule.

With respect to the dimers in accordance with the present invention, in their simpliest form they would comprise the condensation product of a molecule of glutaraldehyde with two molecules of allantoin in which the terminal —CHO groups of the glutaraldehyde reacted with corresponding or different nitrogens in the two allantoin molecules. Thus, in the simplest form just illustrated, the dimer can be defined as comprising a condensation product of glutaraldehyde and allantoin in which two allantoin moieties are linked at corresponding or different nitrogen atoms by a bridge comprising —CH(OH)CH$_2$CH$_2$CH$_2$CH(OH)—, i.e. glutaraldehyde to allantoin ratio is 0.5:1.

In a similar manner, higher polymers within the concept of the general formula given above include those in which more than two allantoin moieties are linked by separate bridges, such as, —CH(OH)CH$_2$CH$_2$CH$_2$CH(OH)— which connect corresponding or different nitrogens in the allantoin molecules or, as shown above in the definitions of the radical, R, following the general formula, a polymer may comprise a five-carbon chain (the residue of the glutaraldehyde molecule) having two allantoin moieties connected to each of the end —CH— groups of the carbon chain. Further included within the concept of the term, "polymer", as used in the claims below, are compounds in which one or more of the allantoin moieties has at least one R-substituent which is the residue of a glutaraldehyde molecule.

Compounds falling within the scope of the foregoing general formula are also capable of forming salts with both acids and bases.

DESCRIPTION OF THE PREFERRED EMBODIMENTS

The preferred compounds are those resulting from the reactions of glutaraldehyde with allantoin in ratios of about 0.5:1 to 4:1, respectively. These compounds and mixtures thereof, as may exist in the reaction products, are useful as antimicrobial additives in compositions for human, agricultural, and industrial uses, in which an effective amount of the compound as an essential active ingredient, optionally combined with a suitable carrier, is added to the composition to be protected.

More specifically, the new compounds, including their salts with acids and bases, can be used as valuable antimicrobial additives for any substance normally subject to spoilage by microorganisms selected from the group consisting of bacteria, yeasts and molds. They may be used as preservative agents in the fields of cosmetics, pharmaceuticals, foods, industrial products, and elsewhere where it is desired to add an antimicrobial agent. They may also be used for disinfectant and sterilizing purposes. Representative uses include, for example, use as additives in industrial products such as textiles, paints, glues, or cutting oils, embalming fluid, etc.; household products such as dishwashing compositions, floor wax emulsions, floor polishes, or laundry starches; cosmetic preparations such as hair preparations, lotions, or shampoos; foodstuffs, such as fruits, vegetables, milk, eggs, meat, grains, cereal products; animal feeds and forage products; by-products or wastes that contain potentially valuable carbohydrates and/or proteins; as a disinfectant on surfaces such as floors, table tops, operating room walls and tables, etc.; as a sterilant for medical and dental instruments, equipment, etc., and for sanitation purposes in cleaning compositions for restaurants, dairies, food plants, kennels, bird cages, slaughter houses, and the like. Other applications will readily suggest themselves to those employed in the relevant arts.

One mode of utilization of the novel compounds of this invention is by adding, as an essential active preservative ingredient, a minor but effective amount of the glutaraldehyde-allantoin reaction products to the compositions to be protected. The latter then become the carrier for the active antimicrobial agent. Since the compounds are generally water soluble, they can be added to cleaning and sanitizing solutions, or they can be added in the form of dry powders as the essential active anti-microbial agent to powdered compositions which are intended either to be used dry or to be dissolved prior to use. Similarly, in the case of cosmetic creams or lotions, the compounds of the present invention can be added during the production process and emulsified into the cosmetic composition which then serves as the carrier for the active anti-microbial agent.

In all of the instances mentioned above only by way of illustration, the effective amount will vary with the intended use. Generally, for preservation purposes, about 0.5% or less by weight, based upon the weight of the material to be protected, will be effective. Solutions of higher concentration may be required for disinfectant or sterilizing purposes and in embalming fluids, e.g. 3% by weight or higher. However, it is entirely within the skill of the art for one working in any given field to readily determine by simple tests the most desirable proportions which would constitute an effective amount.

Especially preferred are those condensation products obtained by reacting glutaraldehyde with allantoin in the ratios of 4:1, 3:1, 2:1, and 1.5:1, respectively. The resulting products can be used by themselves as the only preservative additive in a given composition or they can be used in combination with other preservatives.

Without being limited thereby, the following examples illustrate the production of several representative novel compounds in accordance with the present invention.

EXAMPLE I

A slurry mixture of 39.5 g. (0.25 mole) of allantoin in 50 g. (0.25 mole) of 50% glutaraldehyde plus 250 g. of water was stirred at room temperature, and 11.8 g (0.15 mole) of 50% aqueous sodium hydroxide was added slowly over two hours. The slurry was stirred at room temperature for an additional three hours, and then at 50° C. for a further three hours. The clear colorless solution of 1:1 condensation product was stable on standing at room temperature.

EXAMPLE II

A stirred white slurry of 39.5 g. (0.25 mole) of allantoin in 75.1 g. (0.375 mole) of 50% glutaraldehyde and 226 ml. of water was stirred and heated to 50° C. Addition of 5.39 g. (0.067 mole) of 50% sodium hydroxide dropwise over about one hour, following by stirring at 50° C. for an additional hour, gave a clear solution of the 1:1.5, allantoin-glutaraldehyde condensation product.

EXAMPLE III

A mixture of 79 g. (0.50 mole) of allantoin in 200 g. (1.0 mole) of 50% glutaraldehyde plus 400 g. of water was treated with 10 g. (0.125 mole) of 50% sodium hydroxide over two hours with stirring. After standing at room temperature overnight, an additional 1.15 g. (0.014 mole) of 50% sodium hydroxide was added over one hour with stirring. Unreacted allantoin was removed by filtration, washed with water, and dried, to give 3.85 g. (5% of starting allantoin) m.p. 226°–228° dec., Anal. Found: N,35.21%.

EXAMPLE IV

A slurry of 47.4 g. (0.3 mole) of allantoin and 1.23 g. (0.015 mole) of sodium bicarbonate in 20 g. (0.10 mole) of 50% glutaraldehyde and 400 g. of water was stirred overnight at room temperature. Insoluble material was removed by filtration and dried, giving 38.7 g. of unreacted allantoin, m.p. 227°–228° dec., Anal. Found: N,35.21%. [Anal. Calc'd. for allantoin: N,35.44%]. The filtrate (pH 7.3) contained 1:2 allantoin-glutaraldehyde condensation product.

EXAMPLE V

A slurry of 39.5 g. (0.25 mole) of allantoin in 100 g. (0.50 mole) of 50% glutaraldehyde plus 100 g. of water was warmed to 50° C. and treated with 2.9 g. (0.036 mole) of 50% aqueous sodium hydroxide. The clear solution (pH 7.3) of 1:2 condensation product was stable on standing at room temperature.

EXAMPLE VI

A mixture of 395 g. (2.5 moles) of allantoin in 1500 g. (7.5 moles) of 50% glutaraldehyde plus 1500 g. of water was treated at room temperature with 21.0 g. (0.26 mole) of 50% aqueous sodium hydroxide over 2 hours with stirring. The pH was maintained at approximately 7-8 during the alkali addition, and the slurry gradually changed to a solution after 3 more hours of stirring. The solution was filtered, and water was removed to give the 1:3 allantoin-glutaraldehyde condensation product as a white solid, m.p. 122°–123° dec., Anal. Found: N,13.03%. The condensation product was soluble one part in two parts of water.

EXAMPLE VII

A solution of 7.9 g (0.05 mole) of allantoin in 30 g. (0.15 mole) of 50% glutaraldehyde was treated with two drops of 50% sodium hydroxide and stirred at 50°-60° C. for one hour. The clear, viscous solution was allowed to stand overnight at room temperature, and then diluted with acetone. The white solid allantoin-glutaraldehyde condensation product which precipitated had a nitrogen content of 13.35%.

EXAMPLE VIII

A slurry of 296.3 g (1.875 mole) of allantoin in 1500 g. (7.5 moles) of 50% glutaraldehyde plus 1125 g. of water was treated over one hour with 18.0 g. (0.225 mole) of 50% sodium hydroxide. The slightly hazy solution was filtered, and water was removed from the clear filtrate to give the 1:4 allantoin-glutaraldehyde condensation product as a white solid, m.p. 125°-126° dec., Anal. Found: N,11.25%.

cial Methods of Analysis", 12th Edition, Association of Official Analytical Chemists, Washington, D.C. 1975, pp. 57–65] and has been described in detail previously [Ref: Berke and Rosen, J. Soc. Cosmet. Chem. 29, 757 (1978)]. In general, an inoculum of approximately $10^6$ organisms per ml. was added to a 0.5% test solution of allantoin-glutaraldehyde condensation product, and the mixture was incubated at 35° C. in the case of bacteria (P. aeruginosa, E. coli, S. aureus) or yeast C. albicans), and at 25° C. in the case of mold (A. niger). Samples were taken from the incubated test solution after 1, 2, 3 and/or 7 days and subcultured into AOAC Letheen Broth to determine if any of the microorganisms survived. The following table lists results of subcultures on tests carried out on several of the above-described allantoin-glutaraldehyde condensation products. Growth in the subculture (+) indicates survival of some microorganisms, whereas no growth in the subculture (0) indicates the absence (or less than 10 organisms/ml) of microorganisms in the test solution.

| Product from Example | Allantoin-glutaralde-hyde Cond. product | P. aeruginosa ATCC 9027 1 2 3 7 | E. coli ATCC 8739 1 2 3 7 | S. aureus ATCC 6538 1 2 3 7 | C. albicans ATCC 10231 1 2 3 7 | A. niger ATCC 16404 1 2 3 7 |
|---|---|---|---|---|---|---|
| I | 1:1 | + + + + | | 0 0 0 | | |
| II | 1:1.5 | 0 0 0 | 0 0 0 | 0 0 0 | 0 0 0 | + + 0 0 |
| V | 1:2 | 0 0 0 | | 0 0 0 | | |
| VI | 1:3 | 0 0 0 | 0 0 0 | 0 0 0 | 0 0 0 | + 0 0 0 |
| VIII | 1:4 | 0 0 0 | 0 0 0 | 0 0 0 | 0 0 0 | 0 0 0 0 |

EXAMPLE IX

The following experiment was carried out in the absence of catalyst, producing a 1:4 allantoin-glutaraldehyde condensation product:

To a solution of 80.0 g. (0.40 mole) of 50% glutaraldehyde in 127.0 ml of water was added 15.8 g. (0.10 mole) of allantoin. The slurry was stirred overnight at room temperature, changed gradually to a clear solution of 1:4 allantoin-glutaraldehyde condensation product.

The following examples illustrate the production of products providing a glutaraldehyde to allantoin ratio of 0.5:1. The examples given here were carried out either in the absence of catalyst or in the presence of a small amount of sulfuric acid:

EXAMPLE X

A slurry mixture of 3.16 g. (0.02 mole) of allantoin and 2.0 g (0.01 mole) of 50% glutaraldehyde in 300 ml. of water was stirred for one hour at room temperature. After the slurry had changed gradually to a thin suspension, the reaction mixture was heated briefly at 45° C., giving a clear solution of 2:1 allantoin-glutaraldehyde condensation product.

EXAMPLE XI

A slurry mixture of 3.16 g. (0.02 mole) of allantoin and 2.0 g. (0.01 mole) of 50% glutaraldehyde in 95 ml. of water was treated with 3 drops of concentrated sulfuric acid and heated to 70° C. After a few minutes the slurry changed to a clear solution of 2:1 allantoin-glutaraldehyde condensation product. The solution remained clear on standing and cooling to room temperature.

EXAMPLE XII

The test procedure used was a modification of a phenol coefficient prcedure in common useage [Ref: "Offi-

EXAMPLE XIII

Antimicrobial activity of allantoin-glutaraldehyde condensation product used in combination with other anti-microbial materials.

The test procedure used was the same as the one described in Example XII. In this case, the test solution consisted of 0.3% allantoin-glutaraldehyde condensation product as described in Example VI plus 0.2% methylparaben plus 0.1% propylparaben. The following table lists results of subcultures of the incubated test solution which had been inoculated with ca $10^6$ organisms per ml. of Aspergillus niger (ATCC 9642)

| | A. niger (ATCC 9642) | | | |
|---|---|---|---|---|
| | 1 | 2 | 3 | 7 |
| Test solution | 0 | 0 | 0 | 0 |

Although the novel compounds and their production were described above by specific examples in accordance with the invention, it will be readily apparent to those skilled in the art that these examples are illustrative only and should not be considered to be a limitation on the scope and extent of the invention. Other proportions, catalysts, or reaction conditions can be utilized without departing from the spirit of the invention which is, therefore, not to be considered limited except as defined in the following claims.

I claim:

1. An antimicrobial reaction product of glutaraldehyde and allantoin.

2. The reaction product of claim 1 wherein said reaction product is the result of reaction of glutaraldehyde and allantoin in a ratio in the range of about 0.5:1 to about 4:1, respectively.

3. The reaction product of claim 2 wherein said reaction product is the result of a reaction between glutaraldehyde and allantoin in the presence of a basic catalyst.

4. The reaction product of claim 2 wherein said reaction product is the result of a reaction between glutaraldehyde and allantoin in the absence of a catalyst.

5. The reaction product of claim 2 wherein said reaction product is the result of a reaction between glutaraldehyde and allantoin in the presence of an acid catalyst.

6. An antimicrobial compound selected from the following:

reaction products of allantoin and glutaraldehyde having the formula

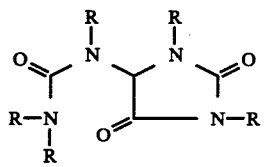

wherein each R is selected from the group consisting of hydrogen and —CHOH(CH$_2$)$_3$CHO, with the proviso that all of the R's are not hydrogen; the carbinolamine dehydration derivatives of said compounds; the dimers and polymers of said compounds; and the salts of said compounds with acids and bases.

7. A compound as defined in claim 6 wherein each R is selected from the group consisting of H—, —CH(OH)—CH$_2$CH$_2$CH$_2$CHO, —CH(OH)CH$_2$CH$_2$CH$_2$CH(OH)—allantoin, —CH(allantoin)CH$_2$CH$_2$CH$_2$CHO, —CH(allantoin)CH$_2$CH$_2$CH$_2$CH(OH)—allantoin, —CH(allantoin)CH$_2$CH$_2$CH$_2$CH(allantoin)$_2$.

8. A compound in accordance with claim 6 wherein the glutaraldehyde to allantoin ratio is within the range of about 0.5:1 to 4:1, respectively.

9. A monomeric reaction product in accordance with claim 6 selected from the group consisting of compounds wherein at least one R is —CH(OH)CH$_2$CH$_2$CH$_2$CHO and compounds in which the terminal —CHO group of said R substituent has reacted with the same or a different nitrogen atom in the same allantoin molecule.

10. A dimeric reaction product in accordance with claim 6 selected from the group consisting of (a) compounds wherein two allantoin molecules are linked at corresponding or different nitrogen atoms by a bridge comprising —CH(OH)CH$_2$CH$_2$CH$_2$CH(OH)—, and (b) dimers as in (a) just preceding wherein one or more nitrogen atoms of at least one of the allantoin molecules has condensed with additional glutaraldehyde.

11. A compound in accordance with claim 6 selected from the group consisting of glutaraldehyde-allantoin condensation products wherein the glutaraldehyde to allantoin ratio is about 4:1, 3:1, 2:1, and 1.5:1.

12. A preserved composition of matter consisting essentially of a major proportion of a substance normally subject to spoilage by microorganisms selected from the group consisting of bacteria yeasts and molds, and a minor proportion effective to inhibit growth of said microorganisms, of a reaction product of glutaraldehyde and allantoin as claimed in claim 1.

13. The composition of claim 12 wherein the ratio of glutaraldehyde and allantoin in said reaction product is in the range of about 0.5:1 to about 4:1, respectively.

14. The composition of claim 12 wherein said reaction product is of the formula

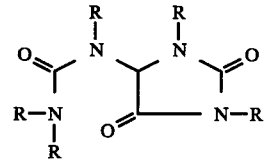

wherein each R is selected from the group consisting of hydrogen and —CHOH(CH$_2$)$_3$CHO, with the proviso that all of the R's are not hydrogen; the carbinolamine dehydration derivatives of said compounds; the dimers and polymers of said compounds; and the salts of said compounds with acids and bases.

15. A solution for use as a disinfectant, sterilant, sanitizer or embalming fluid comprising at least 3% by weight of a reaction product of glutaraldehyde and allantoin as claimed in claim 1 and water.

* * * * *